United States Patent [19]  [11] 4,325,863
Hinsken et al.  [45] Apr. 20, 1982

[54] BENZOFURANONE OR INDOLINONE COMPOUNDS USEFUL AS STABILIZERS FOR ORGANIC MATERIALS

[75] Inventors: Hans Hinsken, Kandern, Fed. Rep. of Germany; Horst Mayerhoefer, Oberwil; Wolfgang Mueller, Allschwil, both of Switzerland; Hermann Schneider, Grenzach-Wyhlen, Fed. Rep. of Germany

[73] Assignee: Sandoz Ltd., Basel, Switzerland

[21] Appl. No.: 118,054

[22] Filed: Feb. 4, 1980

[30] Foreign Application Priority Data

Sep. 5, 1979 [CH] Switzerland .................. 1104/79
Sep. 28, 1979 [CH] Switzerland .................. 8793/79

[51] Int. Cl.$^3$ ................ C08K 5/15; C08K 5/34
[52] U.S. Cl. .................................. 624/111; 524/94; 524/718; 524/728; 524/722; 524/753
[58] Field of Search ................ 260/45.8 A, 45.8 N

[56] References Cited

U.S. PATENT DOCUMENTS

| | | | |
|---|---|---|---|
| 2,535,058 | 12/1950 | Gleim et al. | 260/45.8 A |
| 2,968,645 | 1/1961 | Sterling | 260/45.8 A |
| 3,026,264 | 3/1962 | Rocklin et al. | 260/45.95 B |
| 3,043,775 | 7/1962 | Coffield et al. | 260/45.95 B |
| 3,275,595 | 9/1966 | Breslow | 260/45.8 A |
| 3,325,499 | 6/1967 | Poos | 260/45.8 N |
| 3,370,063 | 2/1968 | Suh | 260/45.8 N |
| 3,428,649 | 2/1969 | Plostnieks | 260/45.8 N |
| 3,471,427 | 10/1969 | Dickson, Jr. | 260/45.8 A |
| 3,577,430 | 5/1971 | Plostnieks | 260/45.8 N |
| 3,862,133 | 1/1975 | Layer | 260/45.8 A |
| 4,080,360 | 3/1978 | Schlichting et al. | 260/45.8 N |
| 4,132,703 | 1/1979 | Crochemore et al. | 260/45.8 A |

*Primary Examiner*—John Kight, III
*Assistant Examiner*—R. A. White
*Attorney, Agent, or Firm*—Gerald D. Sharkin; Robert S. Honor; Joseph J. Borovian

[57] ABSTRACT

The present invention relates to a process for stabilizing organic polymeric materials comprising incorporating therein a benzofuran (2) one or indolin (2) one compound as stabilizer. Such stabilized polymeric materials are stabilized against degradation during the polymer processing.

24 Claims, No Drawings

BENZOFURANONE OR INDOLINONE COMPOUNDS USEFUL AS STABILIZERS FOR ORGANIC MATERIALS

The present invention relates to a process for stabilizing organic polymeric materials employing benzofuranone or indolinone compounds as stabiliser.

Accordingly, the present invention provides a process for stabilising organic polymeric materials comprising incorporating therein a compound of formula $I_c$,

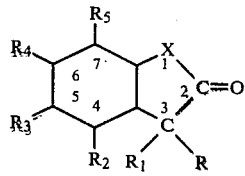

in which either
R is hydrogen,
and $R_1$ is hydrogen; $C_{1-22}$alkyl; $C_{5-6}$cycloalkyl; $C_{1-5}$alkyl-$C_{5-6}$cycloalkyl; phenyl; phenyl substituted by a total of up to three substituents selected from the group consisting of $C_{1-12}$alkyl (up to three of these with max. 18 carbon atoms in the combined alkyl substituents), hydroxyl (max. of two of these), $C_{1-12}$alkoxy, $C_{1-18}$acyloxy, chlorine and nitro (max. of one of each of these); a group of formula (a/4), (a/5) or (a/6)

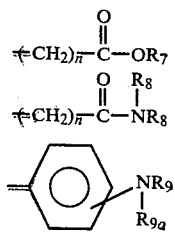

or R and $R_1$ together form a group (a/2)

X is —O— or

with the proviso that when X is

$R_1$ is other than (a/5),
either,
each of $R_2$, $R_3$, $R_4$ and $R_5$, independently, is hydrogen; $C_{1-12}$alkyl;
max. two of $R_2$ to $R_5$ are:
$C_{5-6}$cycloalkyl; $C_{1-5}$alkyl-$C_{5-6}$cycloalkyl; hydroxyl; $C_{1-22}$alkoxy; phenoxy optionally substituted by up to two $C_{1-12}$alkyl groups with a total of up to 16 carbon atoms in the combined alkyl substituents; $C_{1-18}$-acyloxy; phenylcarbonyloxy; chlorine; max. one of $R_2$ to $R_5$ is:
phenyl-$C_{1-9}$alkyl or phenylthio in which the phenyl nucleus is optionally substituted by up to three substituents selected from $C_{1-12}$alkyl, hydroxyl, and $R_{15}CO$—O—; phenyl optionally substituted by up to two $C_{1-12}$alkyl groups with a total of up to 16 carbon atoms in the combined substituents; nitro; 2-furanyl- or 2-thienylcarbonyloxy;

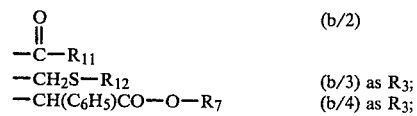

(a/4); or (a/5) as $R_3$ or $R_5$, with the proviso that when R and $R_1$ are hydrogen $R_2$ to $R_5$ are other than hydroxyl, and when $R_{11}$ in (b/2) is other than hydrogen such (b/2) group is adjacent to a hydroxyl group, or $R_2$ and $R_3$, together form a condensed benzene ring, or $R_3$ and $R_4$, together, when X is —O—, form a furan(2)one ring in which the 3-position bears the groups R and $R_1$ as defined above, or $R_4$ and $R_5$, together form tetramethylene or when X is —O— form a furan(2)one ring in which the 3-position bears the groups R and $R_1$ as defined above, and one of the two remaining substituents $R_2$, $R_3$, $R_4$ and $R_5$ is hydrogen and the other is any one of the significances given for $R_2$ to $R_5$, above, either $R_6$ is $C_{1-18}$alkyl; $C_{5-6}$cycloalkyl; $C_{1-5}$alkyl-$C_{5-6}$cycloalkyl; benzyl; $(C_6H_5)_2CH$; phenyl optionally substituted by one or two $C_{1-12}$alkyl groups (total no. of carbon atoms in combined substituents is max. 16), one hydroxy, one or two methoxy groups, one chlorine or one dimethylamino; 3,5-di-tert.-butyl-4-hydroxyphenyl; β-naphthyl; pyridinyl; 2-furyl;

$$-\overset{O}{\underset{\|}{C}}-OR_7 \quad (c/1); \quad \text{or} \quad -\overset{O}{\underset{\|}{C}}-\overset{R_8}{\underset{|}{N}}-R_8 \quad (c/2)$$

and $R_{6a}$ is hydrogen, $C_{1-18}$alkyl ($C_{5-6}$)cycloalkyl, $C_{1-5}$alkyl-$C_{5-6}$cycloalkyl, phenyl or benzyl, or, $R_6$ and $R_{6a}$ together with the C-atom to which they are bound form a 5- or 6-membered aliphatic ring which is optionally substituted by a $C_{1-4}$alkyl group, each $R_7$, independently, is hydrogen; $C_{1-18}$alkyl; alkyl-O-alkylene with a total no. of up to 18 carbon atoms; alkyl-S-alkylene with a total no. of up to 18 carbon atoms; di-$C_{1-4}$-alkylamino$C_{1-8}$alkyl; $C_{5-7}$cycloalkyl; or phenyl optionally substituted by up to 3 $C_{1-12}$alkyl groups with a total no. of up to 18 carbon atoms in the combined substituents;

either, each $R_8$, independently, is hydrogen; $C_{1-18}$alkyl; $C_{5-6}$cycloalkyl; $C_{1-5}$alkyl-$C_{5-6}$cycloalkyl; phenyl optionally substituted by up to two $C_{1-12}$alkyl groups with max. 16 carbon atoms in the combined substituents;

—CH$_2$CH$_2$OH (d/1);
—CH$_2$CH$_2$OC$_{1-18}$alkyl (d/2); or
—CH$_2$CH$_2$—O—$\overset{O}{\underset{\|}{C}}$—R$_{11}$ (d/3)

or, both $R_8$ together with the nitrogen form piperidine or morpholine, $R_9$ has one of the significances of $R_8$, $R_{9a}$ is hydrogen, $C_{1-18}$alkyl, (d/1), (d/2) or (d/3), $R_{10a}$ is hydrogen, $C_{1-18}$alkyl, $C_{5-6}$cycloalkyl, $C_{1-5}$alkyl $C_{5-6}$cycloalkyl, phenyl optionally substituted by up to two $C_{1-12}$-alkyl groups with max. 16 carbon atoms in the combined substituents or benzyl, $R_{11}$ is hydrogen, $C_{1-22}$alkyl, $C_{5-7}$cycloalkyl, phenyl$C_{1-6}$alkyl or phenyl optionally substituted by up to two $C_{1-12}$alkyl groups with max. 16 carbon atoms in the combined substituents.

$R_{12}$ is $C_{1-18}$alkyl, 2-hydroxyethyl, phenyl or $(C_{1-9})$alkylphenyl, $R_{15}$ is $C_{1-22}$alkyl or phenyl, and n is 0, 1 or 2.

When X is $NR_{10a}$ and $R_{10a}$ is phenyl then $R_1$ is preferably an optionally substituted phenyl.

R is preferably hydrogen.

$R_1$ is preferably $R_1'$, where $R_1'$ is hydrogen; $C_{1-18}$alkyl; phenyl optionally substituted by one or two $C_{1-8}$alkyl groups and/or a hydroxyl group; (a/4) or (a/5) or together with R is (a/2). More preferably $R_1$ is $R_1''$, where $R_1''$ is $C_{1-18}$alkyl, or phenyl optionally substituted by one or two $C_{1-8}$alkyl groups and/or a hydroxyl group. Most preferably $R_1$ is phenyl optionally substituted by $C_{1-4}$alkyl, with unsubstituted phenyl being especially preferred.

When $R_1$ is optionally substituted phenyl, such phenyl preferably bears no chlorine atom. When $R_1$ as substituted phenyl bears a hydroxyl group said hydroxyl group is preferably adjacent to a branched alkyl group such as tert.-butyl, more preferably located between two such groups.

When $R_1$ is phenyl substituted by an acyloxy group preferably such group is in the 2- or 4-position and preferably a $C_{1-4}$alkyl group is also present especially in para position to the acyloxy group.

When $R_1$ is optionally substituted phenyl, $R_2$ is preferably hydrogen or methyl, more preferably hydrogen.

When any two of $R_2$ to $R_5$ form a condensed benzene ring, tetramethylene or a condensed furan(2)one ring as defined above preferably both the other substituents are hydrogen or one is hydrogen and the other is $C_{1-4}$alkyl or COOH, most preferably both are hydrogen. When X is

$-NR_{10a}$ the $R_3$ to $R_5$ are preferably other than tert. alkyl groups.

When anyone of $R_2$ to $R_5$ is phenylalkyl or phenylthio in which the phenyl nucleus is substituted as defined above, preferably said phenylalkyl or phenylthio group is $R_3$ or $R_5$, more preferably $R_5$.

Furthermore, when such substituent is present as $R_3$ preferably $R_2$ and $R_4$ are hydrogen and $R_5$ is hydrogen or alkyl (pref. $C_{1-5}$) and when such a substituent is present as $R_5$, preferably $R_2$ and $R_4$ are hydrogen and $R_3$ is hydrogen or alkyl (pref. $C_{1-8}$ especially tert. octyl). Preferred phenylalkyl or phenylthio groups in the case of $R_5$ are those in which the phenyl nucleus has a hydroxy or $R_{15}$ CO—O—substituent in ortho position to the alkyl or thio group. Preferred such groups are:

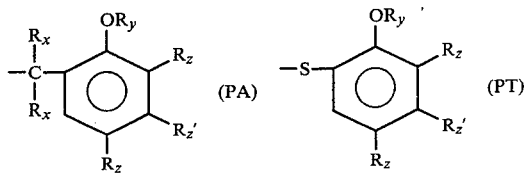

in which each $R_x$, independently, is hydrogen or $(C_{1-4})$-alkyl, $R_y$ is hydrogen or CO-$R_{15}$, and each $R_z$, independently, is hydrogen, $C_{1-9}$-alkyl (linear or branched) and $R_z'$ is hydrogen or $C_{1-4}$ linear alkyl.

In the group (PA) preferably each $R_x$, independently, is hydrogen or $C_{1-4}$alkyl, more preferably hydrogen or methyl; each $R_z$ independently, is preferably hydrogen or $C_{1-4}$alkyl more preferably hydrogen, methyl or tert. butyl with hydrogen or methyl being most preferred. $R_z'$ is preferably hydrogen or methyl, most preferably hydrogen. In the group (PT) each $R_z$, independently, is preferably hydrogen or $(C_{1-8})$alkyl, more preferably, the $R_z$ ortho to $OR_y$ is hydrogen and the other tert. octyl. $R_z'$ is preferably hydrogen.

$R_2$ is preferably $R_2'$, wherein $R_2'$ is hydrogen, $(C_{1-4})$alkyl or together with $R_3'$ forms a condensed benzene ring. More preferably $R_2$ is $R_2''$, where $R_241$ is hydrogen or methyl, especially hydrogen.

$R_3$ is preferably $R_3'$, where $R_3'$ is hydrogen, $C_{1-12}$alkyl, phenyl, $C_{1-18}$alkoxy, phenoxy, $C_{1-18}$alkylcarbonyloxy, (a/4), (a/5), (b/2), (b/4) or together with $R_2'$ forms a condensed benzene ring or together with $R_4'$ forms a furan(2)one nucleus in which R is hydrogen and $R_1$ is preferably $R_1''$. More preferably $R_3$ is $R_3''$, where $R_3''$ is hydrogen, $(C_{1-12})$alkyl, phenyl, (a/4) or together with $R_2'$ forms a condensed benzene ring. Even more preferably $R_3$ is $R_3'''$, where $R_3'''$ is hydrogen, $(C_{1-9})$alkyl or (a/4). Most preferably $R_3$ is $R_3''''$, where $R_3''''$ is hydrogen or alkyl $C_{1-9}$(preferably $C_{1-5}$), with methyl, tert.-butyl or tert.-amyl being most preferred.

When $R_3'$ forms a furanone ring together with $R_4'$ the oxygen atom of said nucleus is preferably bound to the $R_4'$ position. When $R_3$ is (b/2) and $R_{11}$ is other than hydrogen the adjacent hydroxyl group is preferably in the 6-position.

$R_4$ is preferably $R_4'$, where $R_4'$ is hydrogen, $C_{1-12}$alkyl, $C_{1-18}$alkoxy, phenoxy or together with $R_3'$ or $R_5'$ forms a furan(2)one ring in which R is hydrogen and $R_1$ is preferably $R_1''$ or $R_4'$ together with $R_5'$ forms tetramethylene. More preferably $R_4$ is $R_4''$, where $R_4''$ is hydrogen $C_{1-12}$alkyl, $C_{1-18}$alkoxy or phenoxy. Even more preferably $R_4$ is $R_4'''$, where $R_4'''$ is hydrogen or $C_{1-12}$alkyl, especially hydrogen. The preferred alkyl groups as $R_4$ are $C_{1-8}$alkyl, more preferably $C_{1-4}$, with methyl and tert.-butyl being the most preferred alkyl groups.

When $R_4'$ together with $R_5'$ forms a furan(2)one nucleus the oxygen atom of said nucleus is preferably bound to the 7-position.

$R_5$ is preferably $R_5'$, where $R_5'$ is hydrogen, $C_{1-12}$alkyl, phenyl, (a/4), (a/5), (PA), (PT) or together with $R_4'$ forms tetramethylene or a furan(2)one ring. More preferably $R_5$ is $R_5''$, where $R_5''$ is hydrogen, $C_{1-12}$alkyl, (PA) or (PT). More preferably $R_5$ is $R_5'''$, where $R_5'''$ is hydrogen or $C_{1-8}$alkyl with alkyl, preferably $C_{1-5}$alkyl, being most preferred. The preferred $C_{1-5}$alkyl groups are methyl, tert.-butyl and tert.-amyl.

When a furan(2)one nucleus is formed by any two of $R_3'$ to $R_5'$ preferably the $R_1$'s are the same. Most preferably they are phenyl.

X is preferably X', where X' is —O— or —$NR_{10a}'$— in which $R_{10a}'$ is hydrogen, $C_{1-12}$alkyl, preferably $C_{1-4}$alkyl, or phenyl. More preferably X is —O—, —N(-$C_{1-4}$alkyl)— or —N($C_6H_5$)—. Most preferably X is O.

When $R_6$ is substituted phenyl, such phenyl is preferably hydroxyphenyl, phenyl substituted by up to two $C_{1-12}$alkyl groups with max. 16 carbon atoms in the combined substituents or 3,5-di-tert.-butyl-4-hydroxyphenyl; more preferably any substituted phenyl as $R_6$ is mono substituted by one $C_{1-12}$-alkyl group or is 3,5-di-tert.-butyl-4-hydroxyphenyl. Preferably any phenyl as $R_6$ is unsubstituted. Any alkyl as $R_6$, preferably contains 1 to 12, more preferably 1 to 8, most preferably 1 to 4 carbon atoms.

$R_6$ is preferably $R_6'$, where $R_6'$ is $C_{1-18}$alkyl, phenyl, 3,5-di-tert.-butyl-4-hydroxyphenyl, (c/1) or together with $R_{6a}$ is cyclohexylidene. More preferably $R_6$ is $R_6''$, where $R_6''$ is $C_{1-12}$alkyl, phenyl, 3,5-di-tert.-butyl-4-hydroxyphenyl or together with $R_{6a}$ and the common C-atom form cyclohexylidene. Most preferably $R_6$ is $R_6'''$, where $R_6'''$ is $C_{1-12}$alkyl or phenyl.

Any alkyl as $R_{6a}$ preferably contains 1 to 12, more preferably 1 to 8, most preferably 1 to 4 carbon atoms, especially methyl.

$R_{6a}$ is preferably $R_{6a}'$, where $R_{6a}'$ is hydrogen, $C_{1-12}$-alkyl or together with $R_6$ and the common C-atom forms cyclohexylidene. Most preferably $R_{6a}$ is hydrogen. When $R_6$ is substituted phenyl or $CH(C_6H_5)_2$ or (c/1) $R_{6a}$ is preferably hydrogen.

$R_7$ is preferably $R_7'$, where $R_7'$ is hydrogen, $C_{1-18}$alkyl, phenyl optionally substituted by up to two $C_{1-12}$alkyl groups with max. 16 carbon atoms in the combined substituents. More preferably $R_7$ is $R_7''$, where $R_7''$ is $C_{1-18}$alkyl, phenyl or $C_{1-12}$alkylphenyl. Most preferably $R_7$ is $C_{1-18}$alkyl, especially $C_{8-18}$alkyl.

Each $R_8$, independently, is preferably $R_8'$, where $R_8'$ is hydrogen, $C_{1-18}$alkyl or both $R_8'$ together with the N-atom form piperidine. More preferably each $R_8$, independently is hydrogen or $C_{1-18}$alkyl. Preferred alkyl groups as $R_8$ are $C_{1-12}$—, preferably $C_{1-8}$—, most preferably $C_{1-4}$alkyl.

$R_9$ is preferably $R_9'$, where $R_9'$ is hydrogen, $C_{1-8}$alkyl or (d/1). More preferably $R_9$ is hydrogen or $C_{1-8}$alkyl. Any alkyl as $R_9$ preferably contains 1 to 8, more preferably 1 to 4 carbon atoms.

$R_{9a}$ is preferably $R_{9a}'$, where $R_{9a}'$ is hydrogen, $C_{1-8}$-alkyl or (d/1). Any alkyl as $R_{9a}$ preferably contains 1 to 8, more preferably 1 to 4 carbon atoms.

$R_{11}$ is preferably $R_{11}'$, where $R_{11}'$ is hydrogen, $C_{1-18}$alkyl or phenyl. $R_{11}$ in (b/2) is preferably phenyl.

Any alkyl as $R_{11}$ preferably contain 4 to 17 carbon atoms.

$R_{12}$ is preferably $R_{12}'$, where $R_{12}'$ is $C_{1-12}$alkyl, phenyl or 4-(alkyl $C_{1-9}$)phenyl.

n in (a/4) or (a/5) as $R_1$ is preferably 1.
n in (a/4) or (a/5) as $R_5$ is preferably 1.
n in (a/4) or (a/5) as $R_3$ is preferably 2.

The preferred cycloalkyl groups are cyclohexyl and methylcyclohexyl, especially cyclohexyl.

Preferred compounds of formula $I_c$ are those in which $R_1$ is $R_1'$, $R_2$ is $R_2'$, $R_3$ is $R_3'$, $R_4$ is $R_4'$, $R_5$ is $R_5'$ and X is —O—. More preferred compounds are those where R is hydrogen, $R_1$ is $R_1''$, $R_2$ is $R_2''$, especially hydrogen, $R_3$ is $R_3''$, preferably $R_3'''$, $R_4$ is $R_4''$ and $R_5$ is $R_5''$. Especially preferred are those compounds where R is hydrogen, $R_1$ is $C_{1-4}$alkylsubstituted phenyl, or phenyl, especially phenyl, $R_2$ is hydrogen, $R_3$ is $R_3''''$, $R_4$ is hydrogen and $R_5$ is $R_5'''$ especially $C_{1-5}$alkyl.

The compounds of formula $I_c$ are either known or may be prepared from available starting materials in accordance with known methods.

The benzofuran (2) one compounds in which both R and $R_1$ are hydrogen are preferably prepared by reacting a compound of formula III

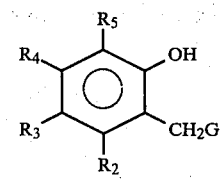

in which $R_2$ to $R_5$ are as defined above with the exception that they are other than (a/5) and that in any group (a/4) or (b/4) present $R_7$ is hydrogen, and G is a secondary amine group of halogen, with an ionic cyanide compound, hydrolising the product thereof, followed by ring closure condensation.

This process forms part of the present invention. G is preferably—$N(C_{1-4})$alkyl$_2$, especially—$N(CH_3)_2$, or morpholine or piperidine. Any halogen as G is preferably chlorine or bromine, especially chlorine. Suitable ionic cyanide compounds are alkali- or alkaline earth cyanides, more preferably sodium- or potassiumcyanide. Each of the reaction steps may be carried out in accordance with known methods for such type of reactions.

It will be appreciated that the end product can be esterified in order to obtain products where $R_7$ is other than hydrogen.

The compounds of formula III are either known or may be prepared in accordance with known methods from available starting materials.

The compounds of formula $I_c$ may be incorporated into the polymeric material to be stabilized before, during, or after polymerization.

The amount of compound of formula $I_c$ incorporated may vary according to the material to be stabilized and the ultimate use to which it is to be put. Suitable amounts are from 0.01 to 5% preferably from 0.05 to 1%, based on the weight of the materials to be stabilized. The organic polymeric materials to be stabilized may be natural or synthetic polymeric materials. Examples of such materials include rubber, polyolefins, especially polyethylene, polypropylene, ethylene, propylene copolymers, polybutylene, polystyrene, chlorinated polyethylene, PVC, polyester, polycarbonate, polymethylmethacrylate, polyphenyleneoxide, polyamides such as nylon, polyurethanes, polypropyleneoxide, phenol-formaldehyde resins, epoxy resins, polyacrylonitrile and corresponding copolymers such as acrylonitrile butadiene styrene (ABS) terpolymers.

The process of the present invention is preferably employed to stabilise polypropylene, polyethylene, ethylene/propylene copolymers, PVC, polyesters, polyamides, polyurethanes, polyacrylonitrile, ABS terpolymers, terpolymers of acrylic ester, styrene and acrylonitrile, copolymers of styrene and acrylonitrile and styrene/butadiene copolymers. The most preferred organic polymeric materials are polypropylene, polyethylene especially HDPE, ethylene/propylene copolymers and ABS.

The incorporation of the compounds of formula $I_c$ in the material to be stabilized is effected in accordance with known methods. Preferred methods are those in which the compounds of formula $I_c$ are incorporated in the polymeric material by melt blending the stabiliser and the additives in conventional equipments such as Banbury mixers, extruders etc. Polypropylene and polyethylene granulates on powders are advantageously employed, whereby the compounds of formula $I_c$ are admixed with said powders and then extruded etc and worked into the films, foils, bands threads etc.

The process of the present invention may be carried out by incorporating a compound of formula $I_c$ alone or together with other additives e.g. further stabilisers etc.

The preferred process according to the present invention comprises incorporating a compound of formula $I_c$ and either (i) a stabiliser of the sterically hindered phenol type, or (ii) a sulphur-containing or phosphorous containing stabiliser, or (i) and (ii), into the polymeric material.

The ratio of stabiliser (i) or (ii) to the compounds of formula $I_c$ incorporated in the polymeric material is suitably 5:1 to 1:5, preferably 2:1 to 1:1. The ratio of combined (other) stabilisers to compounds of formula $I_c$ is suitably 15:1 to 1.5, preferably 6:1 to 1:3. Preferably, when only stabilisers (i) are employed with the compounds of formula $I_c$ the ratio of compounds (i) to those of formula $I_c$ is 3:1 to 1:1.

Examples of sterically hindered phenols are: - β-(4-hydroxy-3,5-ditert.-butylphenyl)-propionicacidstearylester, tetrakis[methylene-3(3',5'-ditert.-butyl-4-hydroxyphenyl)-propionate]-methane, 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazine-2,4,6-(1H,3H,5H)-trione, bis(4-tert.-butyl-3-hydroxy-2,6-dimethylbenzyl)-dithiolterephthalate, tris(3,5-ditert.-butyl-4-hydroxybenzylisocyanurate, triester of 3,5-di-tert.-butyl-4-hydroxyhydrocinnamic acid with 1,3,5-tris(2-hydroxyethyl)-s-triazin-2,4,6-(1H,3H,5H)-trione,bis [3,3-bis-4'-hydroxy-3-tert.-butylphenyl)-butaneacid]-glycolester, 1,3,5-trimethyl-2,4,6-tris-(3,5-ditert.-butyl-4-hydroxybenzyl)-benzene, 2,2'-methylene bis (4-methyl-6-tert.-butylphenyl) terephthalate, 4,4-methylene-bis-(2,6-ditert.-butylphenol), 4,4'-butylidene-bis(6-tert.-butyl-meta-cresol), 4,4-thio-bis(2-tert.-butyl-5-methylphenol), 2,2'-methylene-bis(4-methyl-6-tert.-butylphenol.

Examples of sulphur containing stabilisers are distearylthiodipropionate, dilaurylthiodipropionate, tetrakis(methylene-3-hexylthiopropionate)-methane, tetrakis (methylene-3-dodecylthiopropionate)-methane and dioctadecyldisulphide.

Examples of phosphorous containing compounds are trinonylphenylphosphite, 4,9-distearyl-3,5,8,10-tetraoxadiphospaspiroundecane,tris-(2,4-ditert.-butylphenyl)-phosphite and tetrakis(2,4-ditert.butylphenyl)-4,4'-diphenylene diphosphonite.

In addition to the above further stabilisers, U.V. absorbers as described in DOS 2 606 358 e.g. 2-(2'-hydroxyphenyl)-benztriazole, 2-hydroxybenzophenone, 1,3-bis(2-hydroxybenzoyl)benzene, salicylates, cinnamic acid esters, hydroxybenzoic acid esters, sterically hindered amines and oxylic acid diamides. Suitable such compounds are described in DOS No. 2 606 358.

Metal deactivators for example N,N'-dibenzoylhydrazide, N-benzoyl-N'-salicyloylhydrazide, N,N'-distearylhydrazide, N,N'-bis-[3-(3,5-ditert.-butyl-4-hydroxyphenyl)-propionyl]hydrazide, N,N'-bis-salicyloylhydrazide, oxalylbis-(benzylidenehydrazide), N,N'-bis(3-methoxy-2-naphthoyl-)hydrazide, N,N'-di-α-phenoxy-butyloxy (isophthalyl-dihydrazide) may also be incorporated into the polymeric material.

Additional conventional additives may also be employed for example, flame retardants, antistatic agents etc.

Furthermore, an optical brightener may be incorporated in the polymer to be stabilised and so that the distribution of the additives which are intimately admixed with said optical brightener may be ascertained by fluorescence intensity measurements.

The present invention also provides master batches of polymeric organic materials containing 5 to 90%, preferably 20 to 60%, more preferably 20–30% of a compound of formula $I_c$. Such master batches may then be admixed with unstabilised polymeric material. It is to be appreciated that such master batches may also contain additional additives such as those stated above.

Polymeric materials containing a compound of formula $I_c$ are primarily stabilised against degradation during processing. When, of course, other additives such as antioxidants, e.g. above phenols, and U.V. absorbers are also employed together with the compounds of formula $I_c$, the polymeric material has an enhanced long term stability against thermal- and photoxidative degradation.

The following examples further serve to illustrate the invention. In the examples all parts are by weight, and all temperatures are in degrees Centigrade.

EXAMPLE 1

15.2 Parts mandelic acid and 20.6 parts 2,4-di-tert.-butyl phenol are mixed together and heated under a nitrogen atmosphere to 185° for c. 20 hours. Water is distilled off. After cooling, the reaction mixture is dissolved in ether and extracted with an aqueous sodium bicarbonate solution and then with water. After evaporating-off the solvent and recrystallizing from methanol a compound having a melting point of 113°–114° and of the formula of the 4th compound in Table 1 is obtained.

When, instead of 2,4-di-tert.butylphenol, phenol, p-cresol, m-tert.butylphenol, p-tert.butylphenol, 3,5-dimethylphenol, 2,4-di-tert.butyl-5-methylphenol, 2,4-di-tert.amylphenol, 2,4-di-methylphenol, 3-(4-hydroxyphenyl)-propionicacidoctadecylester, 2,5-di-tert.butyl-phenol, m-cresol, 4-phenylphenol, 2-phenylphenol, resorcinolmonomethylether, resorcinol, stearicacid-3-hydroxyphenylester, 4-hydroxybenzoicacidmethylester, 2-tert.butylphenol, o-cresol, 2,4-di-hydroxybenzophenone, 2,4-dihydroxybenzoic acid, β-naphthol, resorcinol and 2,4-di-hydroxybenzoic acid are used and 1 or 2 equivalents of mandelic acid are reacted therewith; Compounds Nos. 1 to 3, 5 to 20 and 22 to 26 are obtained. Compounds Nos. 54 to 61 may be prepared in analogous manner. Compound No. 17 of Table 1 is obtained by esterifying Compound No. 16 with stearicacidchloride; Compound No. 21 by esterifying Compound No. 20 with stearylalcohol in accordance with known methods.

EXAMPLE 2

1.34 Parts of the Compound No. 1 of Table 1, 1.0 part cyclohexanone, 0.02 parts piperidinebenzoate and 20 parts toluene are mixed together and heated for 21 hours under reflux. The mixture is concentrated in a rotation evaporator. Then the residue is dissolved in 120 parts ether, the ether solution washed with water, dehydrated over Glauber's salts and evaporated to dryness. After recrystallization from methanol, white crystals, melting point 74°–75°, of Compound No. 27 of Table 1 are obtained.

Compounds Nos. 28 of Table 1, and 32 and 39 of Table 2 are prepared in analogous manner.

EXAMPLE 3

A solution of 10.14 parts diphenylamine in 40 parts ether is added dropwise to a solution of 5.67 parts α-chlorophenylacetylchloride in 8 parts ether, subsequently 2.92 parts triethylamine are added thereto. The mixture is heated to 40° for 15 hours, the residue is filtered-off and washed with water and ether. White crystals having a melting point of 143°–144° are obtained. 4.82 Parts of the crystalline product are added to 60 parts nitrobenzene and 4 parts aluminium chloride are added slowly portionwise thereto, whereupon the temperature rises to 30° and a clear yellow solution is obtained. After 3 hours the solvent is removed by evaporation and the residue is added to a mixture of 100 parts ice water and 80 parts conc. hydrochloric acid. The product is extracted with ether, then the combined ether solutions are washed with water, dehydrated with MgSO4 and the ether is evaporated. The yellow oil is made crystalline by washing with petroleum ether (m.pt. 96°–98°). The product has the formula of Compound No. 30 of Table 1. Compounds 29 and 31 are made in analogous manner.

EXAMPLE 4

78.9 Parts of the compound of formula

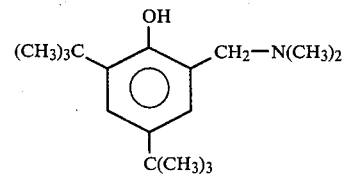

are dissolved in 450 parts diethyleneglycolmonomethylether. 39 Parts potassium cyanide and 6 parts potassium iodide are added thereto. At a temperature of 80°, 63 parts of water are added dropwise. The temperature is raised to 130° and the mixture is stirred for 16 hours at this temperature. After cooling to room temperature, 1000 parts ice water are added. After carefully acidifying with hydrochloric acid, a precipitate is formed which is dissolved in 400 parts ether. The organic phase is separated, washed with water, dehydrated over MgSO4 and evaporated. The residue is added to toluene, heated to the boil for approximately 1 hour whereupon water of condensation separates out. After evaporating the solvent and recrystallizing from methanol a colourless crystalline product, melting point 88°–89°, which is of the formula No. 41 in Table 2, is obtained.

EXAMPLE 5

Using a compound of formula

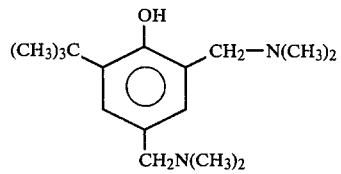

and proceeding in analogous manner to Example 4 Compound No. 42 of Table 2, is obtained.

TABLE 1

| No. | R2 | R3 | R4 | R5 | m.pt. °C. |
| --- | --- | --- | --- | --- | --- |
| 1 | H | H | H | H | 113–115 |
| 2 | H | CH3 | H | H | 103–104 |
| 3 | H | H | —C(CH3)3 | H | 129–130 |
| 4 | H | —C(CH3)3 | H | —C(CH3)3 | 113–114 |
| 5 | H | —C(CH3)3 | H | H | 133–134 |
| 6 | —CH3 | H | —CH3 | H | 99,5–100 |
| 7 | —CH3 | —C(CH3)3 | H | —C(CH3)3 | 147–149 |
| 8 | H | —C(CH3)2(C2H5) | H | —C(CH3)2(C2H5) | oil |
| 9 | H | —CH3 | H | —CH3 | oil |
| 10 | H | —CH2—CH2—C(=O)—O—C18H37 | H | H | 35 |
| 11 | —C(CH3)3 | H | H | —C(CH3)3 | 126–129 |
| 12 | H | H | —CH3 | H | 66–109 |
| 13 | H | phenyl | H | H | 104–106 |
| 14 | H | H | H | phenyl | 112–124 |

TABLE 1-continued

[Structure: cyclohexane fused with lactone ring, R2, R3, R4, R5 substituents, CH-phenyl group]

| No. | R₂ | R₃ | R₄ | R₅ | m.pt. °C. |
|-----|-----|-----|-----|-----|-----|
| 15 | H | H | CH₃O— | H | 126–128 |
| 16 | H | H | OH | H | oil |
| 17 | H | H | —O—C(=O)—C₁₇H₃₅ | H | 68–70 |
| 18 | H | —COOCH₃ | H | H | oil |
| 19 | H | H | H | —C(CH₃)₃ | 129–130 |
| 20 | H | —CH(phenyl)—COOH | H | —CH₃ | oil |
| 21 | H | —CH(phenyl)—COOC₁₈H₃₅ (substituent shown with CH-phenyl and COOC₁₈H₃₅) | H | —CH₃ | wax |
| 22 | H | —C(=O)—phenyl | OH | H | 143–145 |
| 23 | H | —COOH | OH | H | oil |

No. 24 [naphthalene fused lactone with CH-phenyl] m.pt. 181–183°

No. 25 [benzene with two fused lactone rings each bearing CH-phenyl] oil

No. 26 [benzene ring with HOOC, two fused lactone rings each with CH-phenyl] m.pt. 64–65°

No. 27 [benzo-fused lactone with =CH-cyclohexyl] m.pt. 74–75°

No. 28 [benzo-fused lactone with =CH-phenyl] m.pt. 76–78°

No. 29 [N-methyl benzo-fused lactam with CH-phenyl] m.pt. 114–116°

TABLE 1-continued
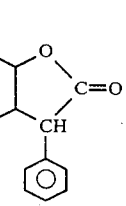
| No. | R₂ | R₃ | R₄ | R₅ | m.pt. °C. |
|---|---|---|---|---|---|
| No. 30 | | | | | m.pt. 96–98° |
| No. 31 | | | | | m.pt. 182–185° |
TABLE 2
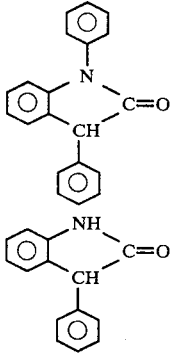
| No. | $R_1$ | R | $R_3$ | $R_5$ | m.pt. °C. |
|---|---|---|---|---|---|
| 32 | =CH—(2,6-(CH₃)₂-4-OH-phenyl) | — | —C(CH₃)₃ | —C(CH₃)₃ | 90–95 |
| 33 | phenyl | H | —C(CH₃)₂—CH₂C(CH₃)₃ | —C(CH₃)₂CH₂C(CH₃)₃ | |
| 34 | 2-HO-5-C₄H₉-phenyl | H | C₉H₁₉ | H | oil |
| 35 | 2-HO-5-CH₃-phenyl | H | CH₃ | H | 203–205 |
| 36 | 2-OH-3,5-(CH₃)₂-phenyl | H | CH₃ | CH₃ | 175 |
| 37 | phenyl | H | H | phenyl | 116–118 |
| 38 | phenyl | H | —CH₂COOC₁₈H₃₇ | —C(CH₃)₃ | oil |
| 39 | =CH—(CH₂)₁₀—CH₃ | H | —C(CH₃)₃ | —C(CH₃)₃ | oil |

TABLE 2-continued structure: benzofuranone with R5 (top), R3 (left), R and R1 (on carbon)

| No. | R₁ | R | R₃ | R₅ | m.pt. °C. |
|---|---|---|---|---|---|
| 40 | OC(=O)—C₁₇H₃₅ on 2,4-dimethylphenyl | H | CH₃ | H | 65–66 |
| 41 | H | H | —C(CH₃)₃ | —C(CH₃)₃ | 88–89 |
| 42 | H | H | —CH₂—COOH | —C(CH₃)₃ | 175–177 |
| 43 | H | H | —CH₂—COOC₁₈H₃₇ | —C(CH₃)₃ | 50–53 |
| 44 | phenyl | H | —CH₂—S—phenyl | —C(CH₃)₃ | oil |
| 45 | phenyl | H | —CH₂—S—C₁₂H₂₅ | —C(CH₃)₃ | oil |
| 46 | cyclohexyl | H | H | H | 74–75 |
| 47 | ⟨CH₂⟩₁₇—CH₃ | H | —C(CH₃)₃ | —C(CH₃)₃ | oil |
| 48 | —CH₂C(=O)—O—C₄H₉ | H | —C(CH₃)₃ | —C(CH₃)₃ | oil |
| 49 | phenyl | H | —C(CH₃)₃ | —CH₂COC₁₈H₃₇ (with C=O) | wax |
| 50 | =CH—C(=O)—O—C₄H₉ | — | C(CH₃)₃ | —C(CH₃)₃ | 70–72 |
| 51 | =CH—CH(C₆H₅)₂ | — | —C(CH₃)₃ | —C(CH₃)₃ | 67–73 |
| 52 | —C₆H₄—OCH₃ | H | —C(CH₃)₃ | —C(CH₃)₃ | 94–97 |
| 53 | —C₆H₄—Cl | H | —C(CH₃)₃ | —C(CH₃)₃ | 121–123,5 |

No. 54 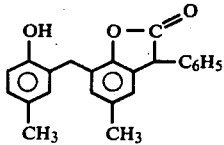 glassy mass

No. 55 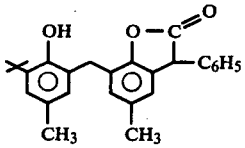 m.pt. 125–129° C.

No. 56 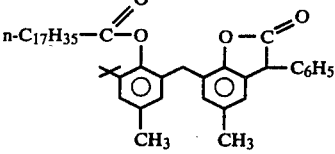 oil

No. 57 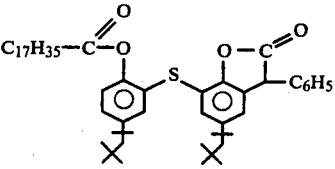 oil

TABLE 2-continued

[Structure: benzofuranone core with R5, R3, R1, R substituents; C=O lactone]

| No. | R₁ | R | R₃ | R₅ | m.pt. °C. |
|---|---|---|---|---|---|
| No. 58 & No. 59 | —CH₂COOR (with O—C(=O) benzofuranone group) | | | 58. R = H m.pt. 175–177°<br>59. R = C₁₈H₃₅ m.pt. 50–53° | |
| No. 60 | [structure: OH-phenyl(t-Bu)₂—S—benzofuranone with C₆H₅] | | | | m.pt. 52–58° |
| No. 61 | [structure: OH-phenyl(t-Bu)₂—CH₂—benzofuranone with C₆H₅] | | | | m.pt. 123–132° |

EXAMPLE A

A mixture of 1200 parts of a commercially available unstabilized polypropylene (Profax 6501), 0.6 parts calciumstearate, 0.6 parts tetrakis-[methylene-3(3′,5′-di-tert.-butyl-4′-hydroxyphenyl)-propionate]-methane and 0.6 parts of the Compound No. 4 of Table 1 are shaken together for 10 minutes and extruded at 120 revs/min with temperatures of 150°, 240°, 260°, and 200° in the different heating areas of the extruder to form a strand which is granulated after passing through a water bath. The granulate is extruded and granulated a further 9 times, each time a part is taken to measure the Melt Flow Index (MFI according to ASTM D 1238 L, 230°; 2.16 kg) which serves as a measure of the thermomechanical oxidative degradation of a polymer. A control without Compound 4 of the Table is also extruded in like manner and tested. In comparison, the polymer containing Compound No. 4 of the Table exhibits a greatly improved melt stability during continuous extrusion. The other compounds of the Table may be employed in like manner.

EXAMPLE B

100 Parts unstabilized HD-polyethylene powder (Phillips Type) are stabilized with 0.02 parts Compound No. 5 of Table 1 and 0.01 parts tetrakis-[methylene-3(3′,5′-di-tert.-butyl-4′-hydroxyphenyl)-propionate]-methane. The powder is subjected to a modified MFI Test at 230°/0.325 kg on a Davenport-MFI apparatus. The powder is pushed into a heated steel cylinder and a 325 g weight is placed thereon. The polymer which is pressed out is cut off at 60 second intervals. The amount is calculated in terms of g/10 min. The stronger the crosslinking of the polymer owing to insufficient stabilization, the lower the MFI value. After 5 to 15 minutes a constant value is obtained. The other compounds of the Tables may be used in analogous manner.

EXAMPLE C 1.0 Part octylstearate, 1.5 parts Ba-Cd stabilizer (powder), 1 part of Compound No. 4 of Table 1 and 0.5 parts of a commercially available arylalkylphosphate are mixed with 100 parts commercially available dispersion PVC (k-value-60) in a Fluid Mixer (Papenmeier Type TEHK8) until the temperature has risen to 110°. The homogeneous mixture is rolled on rollers heated to 180° for 1 minute and then pressed into plates (thickness 1 mm) at 200° for 1.5 min. at 2 atm. and 1.5 minutes at 20 atm. The test or plates are put into an air circulating drying cabinet at 180° for 30 minutes. A comparison sample which contained 2.5 parts Ba-Cd stabilizer instead of Compound No. 4 and 1.5 parts of the Ba-Cd stabilizer was also treated in the same manner. This sample undergoes discolouration even at the beginning of the heat treatment and is markedly more discoloured after the 30 minutes than the sample containing Compound No. 4 of Table 1.

EXAMPLE D

300 Parts ABS powder (Fa. Marbon AOE 30/075) are dissolved in 2200 parts chloroform and the solution is dropped into 8000 parts methanol whereupon the ABS is precipitated. After filtration the polymer which is now free from stabilizer is treated in vacuo overnight to remove all the solvent. 100 parts of the so-treated ABS powder is dissolved in chloroform and 0.2 parts Compound No. 10 of Table 1 are added thereto and the whole is stirred under nitrogen atmosphere for 15 minutes. The solution is drawn into a film with a 1 mm doctor blade onto a glass plate and is left for the solvent to evaporate-off whereby the film shrinks to 150μ thickness, and is freed from the rest of the solvent overnight at room temperature in vacuo. The film is then stoved in an air-circulating oven at 95°. By repeated IR-measurement to Δε=0.4 at 1715 cm⁻¹ the ageing resistance is checked. The samples containing the benzofuranone compound have longer resistance than the control samples which contain no stabilizer.

EXAMPLE E

100 Parts granulated polyethyleneterephthalate are ground to a rough powder and dried overnight at 100° in a vacuum drying cabinet. 1.0 Part of Compound No. 38 of Table 2 is added and the mixture is homogenised, then granulated in an extruder, spun into fibres at 280°, stretched (120 den/14) and twisted. The fibres are wound on to white cards and exposed to the light in an Atlas Weatherometer for 24 hour intervals. In comparison to a non-stabilized control, the sample containing Compound No. 41 has less tendency to yellow during the exposure to light and can be left in the Weatherometer for a substantially longer period of time in order to reach the same decrease in the tensile strength (50%).

EXAMPLE F 49.5 Parts Compound No. 4 of Table 1, 49.5 parts tetrakis-[methylene-3-(3',5'-di-tert.-butyl-4'-hydroxyphenyl)-propionate]-methane, 1 part calcium stearate and 0.02 parts (7-[2H-naphthol(1,2d)triazol-2-yl]-3-phenylcumarine (optical brightener) are heated to 160°. The mixture melts with stirring and the melt is poured into a flat dish and ground after cooling. The product obtained melts at 70°–75°.

0.5 Parts of the ground melt are mixed in a plastic bag by repeated shaking with 1000 parts unstabilized HDPE powder (Ziegler Type, MFI 190/z=0.7). 43 Parts of the powder mixture are heated to 220° in a Brabender Plasti-Corder PLV 151 extruder at 50 revs/min. until there is a sharp drop in the torque indicating polymer degradation. In comparison to a sample stabilized with double the amount of a 1:1 mixture of tetrakis-[methylene-3-(3',5'-di-tert.-butyl-4'-hydroxyphenyl)-propionate]-methane, and 2,6-di-tert.-butyl-4-methylphenol the test sample exhibits superior stability.

When different concentrations of the above melt product are mixed with polyethylene or polypropylene powder and extruded into a strand which are subsequently ground, the fluorescence intensity can be measured to assess the concentration of additives in the polymer.

What is claimed is:

1. A process for stabilizing organic polymeric materials comprising incorporating therein a stabilizing amount of a compound of formula Ic,

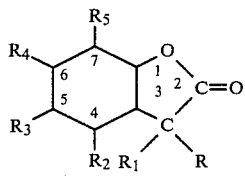

in which either
R is hydrogen, and
$R_1$ hydrogen; $C_{1-22}$ alkyl; $C_5$ or $C_6$ cycloalkyl; $C_{1-5}$ alkyl-$C_5$ or $C_6$ cycloalkyl; phenyl; phenyl substituted by one to three substituents selected from the group consisting of $C_{1-12}$—alkyl, hydroxy, $C_{1-12}$ alkoxy, $C_{1-18}$—acyloxy, chloro or nitro, with the provisos that: (1) when the phenyl ring contains more than one $C_{1-12}$ alkyl group, said alkyl groups contain a maximum of 18 carbon atoms, (2) the maximum number of hydroxy substituents is two, and (3) the maximum number of each of the substituents selected from $C_{1-12}$ alkoxy, $C_{1-18}$ acyloxy, chloro and nitro is one; or a group of formula (a/4), (a/5) or (a/6)

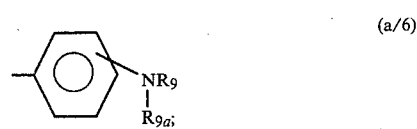

or R and $R_1$ together form a group (a/2)

either
each of $R_2$ to $R_5$, independently, is hydrogen; $C_{1-12}$ alkyl; $C_5$ or $C_6$ cycloalkyl; $C_{1-5}$ alkyl-$C_5$ or $C_6$ cycloalkyl; $C_{1-22}$ alkoxy; phenoxy; phenoxy substituted by one or two $C_{1-12}$ alkyl groups,
said alkyl groups having a maximum of 16 carbon atoms; $C_{1-18}$ acyloxy; chloro; phenyl-$C_{1-9}$ alkyl; phenylthio; phenyl-$C_{1-9}$ alkyl or phenylthio substituted on the phenyl ring by one to three substituents selected from $C_{1-12}$ alkyl, hydroxy and $R_{15}CO$—O—; phenyl; phenyl substituted by one or two $C_{1-12}$ alkyl groups, said alkyl groups having a maximum of 16 carbon atoms; nitro; 2-furanylcarbonyloxy; 2-thienylcarbonyloxy; a group of formula (b/2), (b/3) or (b/4)

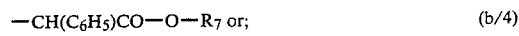

a group of formula (a/4) or (a/5) as defined above; with the provisos that:
(a) a maximum of two of $R_2$ through $R_5$ is $C_5$ or $C_6$ cycloalkyl, $C_{1-5}$ alkyl-$C_5$ or $C_6$ cycloalkyl, $C_{1-22}$ alkoxy, phenoxy, substituted phenoxy, $C_{1-18}$ acyloxy or chloro; and
(b) a maximum of one of $R_2$ through $R_5$ is optionally substituted phenyl, phenyl-$C_{1-9}$ alkyl or phenylthio, nitro, 2-furanylcarbonyloxy, 2-thienylcarbonyloxy or a group of formula (b/2), (b/3), (b/4), (a/4) or (a/5), provided that only the $R_3$ substituent can be a group of formula (b/3) or (b/4) and only the $R_3$ or $R_5$ substituent can be a group of formula (a/5);
or $R_2$ and $R_3$, together, form a condensed benzene ring,
or $R_3$ and $R_4$, together, form a furan(2) one ring in which the 3-position bears the substituents R and $R_1$ as defined above,
or $R_4$ and $R_5$, together, form tetramethylene or a furan(2) one ring in which the 3-position bears the substituents R and $R_1$ as defined above, and one of the two remaining substituents is hydrogen and the other is any one of the significances given for $R_2$ to $R_5$ above;
either
$R_6$ is $C_{1-18}$ alkyl; $C_5$ or $C_6$ cycloalkyl; $C_{1-5}$ alkyl-$C_5$ or $C_6$ cycloalkyl; benzyl; $(C_6H_5)_2CH$; phenyl; phenyl mono- or disubstituted by $C_{1-12}$ alkyl, provided that when the phenyl ring contains more than one $C_{1-12}$ alkyl group, said alkyl groups contain a maximum of 16 carbon atoms; phenyl monosubstituted by hydroxy; phenyl mono- or disubstituted by methoxy; phenyl monosubstituted by chloro; phenyl monosubstituted by dimethylamino; 3,5-di-tertiary butyl-4-hydroxyphenyl; β-naphthyl; pyridinyl; 2-furyl; or a group of formula (c/1) or (c/2)

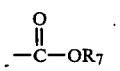  (c/1)

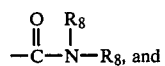  (c/2)

$R_{6a}$ is hydrogen; $C_{1-18}$ alkyl; $C_5$ or $C_6$ cycloalkyl; $C_{1-5}$ alkyl-$C_5$ or $C_6$ cycloalkyl; phenyl or benzyl;
or
$R_6$ and $R_{6a}$, together with the carbon atom to which they are bound, form an unsubstituted 5- or 6-membered aliphatic ring or a 5- or 6-membered aliphatic ring monosubstituted by $C_{1-4}$ alkyl;
each
$R_7$, independently, is hydrogen; $C_{1-18}$ alkyl; alkyl-O-alkylene having a maximum of 18 carbon atoms; alkyl-S-alkylene having a maximum of 18 carbon atoms; di-$C_{1-4}$ alkylamino-$C_{1-8}$ alkyl; $C_{5-7}$ cycloalkyl; phenyl; or phenyl substituted by one to three $C_{1-12}$ alkyl groups, said alkyl groups having a maximum of 18 carbon atoms;
either
each $R_8$, independently, is hydrogen; $C_{1-18}$ alkyl; $C_5$ or $C_6$ cycloalkyl; $C_{1-5}$ alkyl-$C_5$ or $C_6$ cycloalkyl; phenyl; phenyl substituted by one or two $C_{1-12}$ alkyl groups, said alkyl groups having a maximum of 16 carbon atoms; or a group of formula (d/1), (d/2) or (d/3)

—CH$_2$CH$_2$OH  (d/1)

—CH$_2$CH$_2$OC$_{1-18}$alkyl  (d/2)

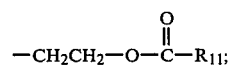  (d/3)

or both
$R_8$'s, together with the nitrogen atom, form an unsubstituted piperidine or morpholine ring;
$R_9$ has one of the significances of $R_8$;
$R_{9a}$ is hydrogen; $C_{1-18}$ alkyl; or a group of formula (d/1), (d/2) or (d/3) as defined above;
$R_{11}$ is hydrogen; $C_{1-22}$ alkyl; $C_{5-7}$ cycloalkyl; phenyl; phenyl-$C_{1-6}$ alkyl; or phenyl or phenyl-$C_{1-6}$ alkyl substituted on the phenyl ring by one or two $C_{1-12}$-alkyl groups, said alkyl groups having a maximum of 16 carbon atoms;
$R_{12}$ is $C_{1-18}$ alkyl; 2-hydroxyethyl; phenyl; or $C_{1-9}$ alkylphenyl;
$R_{15}$ is $C_{1-22}$ alkyl or phenyl;
and n is 0, 1 or 2.

2. A process according to claim 1, in which either $R_6$ is $C_{1-18}$ alkyl, phenyl, 3,5-di-tertiary butyl-4-hydroxyphenyl or a group of formula (c/1), and $R_{6a}$ is hydrogen or $C_{1-12}$ alkyl, or $R_6$ and $R_{6a}$, together with the carbon atom to which they are bound, form a cyclohexylidene ring; each $R_7$, independently, is hydrogen, $C_{1-18}$ alkyl, phenyl or phenyl substituted by one or two $C_{1-12}$ alkyl groups, said alkyl groups having a maximum of 16 carbon atoms; either each $R_8$, independently, is hydrogen or $C_{1-18}$ alkyl, or both $R_8$'s, together with the nitrogen atom, form an unsubstituted piperidine ring; $R_9$ and $R_{9a}$, independently, are hydrogen, $C_{1-8}$ alkyl or a group of formula (d/1); $R_{12}$ is $C_{1-12}$ alkyl, phenyl or $C_{1-9}$ alkylphenyl, wherein the alkyl group is in the 4-position of the phenyl ring; and n in (a/4) or (a/5) as $R_1$ or $R_5$ is 1, and n in (a/4) or (a/5) as $R_3$ is 2.

3. A process according to claim 2, in which either R is hydrogen and $R_1$ is hydrogen, $C_{1-18}$ alkyl, phenyl, phenyl substituted by one to three substituents selected from $C_{1-8}$ alkyl and hydroxy, with the proviso that the maximum number of $C_{1-8}$ alkyl substituents is two and the maximum number of hydroxy substituents is one, or a group of formula (a/4) or (a/5), or R and $R_1$, together, form a group of formula (a/2), where $R_6$, $R_{6a}$, $R_7$, $R_8$ and n are as defined in claim 2; $R_2$ is hydrogen or $C_{1-4}$ alkyl; $R_3$ is hydrogen, $C_{1-12}$ alkyl, phenyl, $C_{1-18}$ alkoxy, phenoxy, $C_{1-18}$ alkylcarbonyloxy, a group of formula (a/4), (a/5), (b/2) or (b/4), where $R_7$, $R_8$ and n are as defined above or, together with $R_2$, forms a condensed benzene ring; $R_4$ is hydrogen, $C_{1-12}$ alkyl, $C_{1-18}$ alkoxy, phenoxy or, together with $R_3$, forms a furan(2)one ring in which the 3-position bears the substituents R and $R_1$, where R is hydrogen and $R_1$ is as defined above; and $R_5$ is hydrogen, $C_{1-12}$-alkyl, phenyl, a group of formula (a/4) or (a/5), where $R_7$, $R_8$ and n are as defined above, a group of formula (PA) or (PT)

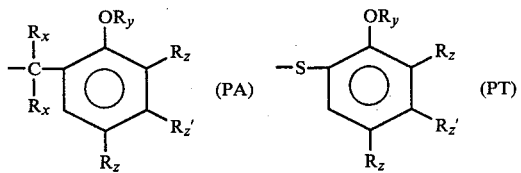

in which
each $R_x$, independently, is hydrogen or $C_{1-4}$ alkyl,
$R_y$ is hydrogen or a group —CO—$R_{15}$, where $R_{15}$ is $C_{1-22}$ alkyl or phenyl,
each $R_z$, independently, is hydrogen or $C_{1-9}$ alkyl, and
$R_z'$ is hydrogen or $C_{1-4}$ linear alkyl, with the proviso that at least one $R_z$ or $R_z'$ must be hydrogen, or, together with $R_4$, forms tetramethylene or a furan(2)one ring.

4. A process according to claim 3, in which when $R_2$ and $R_3$, together, form a condensed benzene ring or $R_3$ and $R_4$, together, form a furan(2)one ring or $R_4$ and $R_5$, together form a furan(2)one ring or tetramethylene, one of the two remaining substituents $R_2$ to $R_5$ is hydrogen and the other is hydrogen, COOH or $C_{1-4}$ alkyl, with the proviso that $R_3$ and $R_5$ cannot be carboxy.

5. A process according to claim 4, in which $R_1$ is $C_{1-18}$ alkyl, phenyl or phenyl substituted by one to three substituents selected from $C_{1-8}$ alkyl and hydroxy, with the proviso that the maximum number of $C_{1-8}$ alkyl substituents is two and the maximum number of hydroxy substituents is one.

6. A process according to claim 5, in which $R_1$ is phenyl or phenyl monosubstituted by $C_{1-4}$ alkyl.

7. A process according to claim 1, in which $R_1$ is p-methoxyphenyl; R, $R_2$ and $R_4$ are hydrogen, and $R_3$ and $R_5$ are tert.-butyl.

8. A process according to claim 1, in which, in the compound of formula $I_c$, where any one of $R_2$ to $R_5$ form a benzene ring or furan(2)one ring or tetramethylene one of the remaining substituents $R_2$ to $R_5$ is hydrogen and the other is hydrogen, COOH or $C_{1-4}$ alkyl.

9. A process according to claim 1 in which any optionally substituted phenylalkyl or phenylthio as $R_2$ to $R_5$ is in the 5- or 7-position.

10. A process according to claim 9, in which when $R_3$ is optionally substituted phenylalkyl or phenylthio, $R_2$ and $R_4$ are hydrogen and $R_5$ is hydrogen or $C_{1-5}$ alkyl and when $R_5$ is optionally substituted phenylalkyl or phenylthio $R_2$ and $R_4$ are hydrogen and $R_3$ is hydrogen or $C_{1-8}$ alkyl.

11. A process according to claim 9, in which any optionally substituted phenylalkyl or phenylthio is in the 7-position.

12. A process according to claim 3, in which when $R_5$ is (PA) or (PT), $R_2$ and $R_4$ are both hydrogen and $R_3$ is hydrogen or $C_{1-8}$ alkyl.

13. A process according to claim 1, in which the polymeric material is polypropylene, polyethylene, ethylene/propylene copolymers, polybutylene, polystyrene, PVC, polyesters, polyamides, polyurethanes, polyacrylonitrile, ABS terpolymers, terpolymers of acrylic ester, styrene and acrylonitrile, copolymers of styrene and acrylonitrile and styrene/butadiene copolymers.

14. A process according to claim 1, in which the polymeric material is polypropylene.

15. A process according to claim 1, in which the polymeric material is polyethylene or an ethylene/propylene. copolymer.

16. A process according to claim 15, in which the polymeric material is high density (HD) polyethylene.

17. A process according to claim 1, in which from 0.01 to 5%, based on the weight of the polymeric material, of a compound of formula Ic is incorporated in the polymeric material to be stabilized.

18. A process according to claim 1, in which a compound of formula Ic is incorporated into the polymeric material by melt blending.

19. Polymeric organic material stabilised with a compound of formula Ic, as defined in claim 1.

20. A process according to claim 1, in which $R_1$ is phenyl and R is hydrogen.

21. A process according to claim 1, in which $R_1$ is phenyl, R, $R_2$ and $R_4$ are hydrogen and $R_3$ and $R_5$ are $C_{1-5}$ alkyl.

22. A process according to claim 21, in which $R_3$ and $R_5$ are methyl, tert.-butyl or tert.-amyl or $R_3$ is methyl and $R_5$ is tert.-butyl.

23. A process according to claim 1 comprising incorporating a compound of formula $I_c$ together with either (i) a stabilizer of the sterically hindered phenol type or (ii) a stabilizer of the thiodipropionate, thiopropionate, dialkylsulphide, aryl phosphite, aryl diphosphonite and tetraoxadiposphaspiroundecane type, or (i) and (ii), into the polymeric material to be stabilized.

24. A process according to claim 1, in which $R_1$ is phenyl; R, $R_2$ and $R_4$ are hydrogen, and $R_3$ and $R_5$ are tert.-butyl.

* * * * *

UNITED STATES PATENT AND TRADEMARK OFFICE
CERTIFICATE OF CORRECTION

PATENT NO. : 4,325,863

DATED : April 20, 1982

INVENTOR(S) : Hinsken et al.

It is certified that error appears in the above-identified patent and that said Letters Patent is hereby corrected as shown below:

Title page, left-hand column, Item [30]; change "Sep. 5, 1979" to -- Feb. 5, 1979 --.

Column 4, line 28; after "where", change "$R_2 41$" to -- $R_2$" --.

Column 6, line 23; after "group", change "of" to -- or --.

Column 11; delete the structural formula at the top of said column and substitute therefor the formula -- 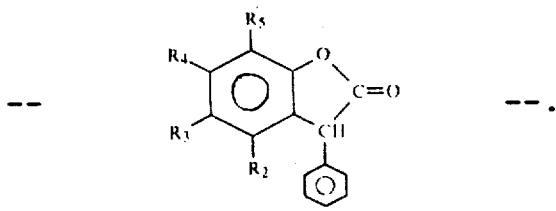 --.

UNITED STATES PATENT AND TRADEMARK OFFICE
CERTIFICATE OF CORRECTION

PATENT NO. : 4,325,863

DATED : April 20, 1982

INVENTOR(S) : Hinsken et al.

It is certified that error appears in the above-identified patent and that said Letters Patent is hereby corrected as shown below:

Column 19, directly beneath line 47; delete the structural formula and substitute therefor the formula -- 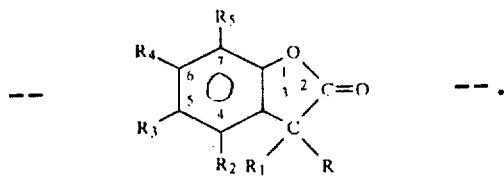 --.

Signed and Sealed this

Twenty-fourth Day of July 1984

[SEAL]

*Attest:*

*Attesting Officer*

GERALD J. MOSSINGHOFF

*Commissioner of Patents and Trademarks*